United States Patent [19]
Yokoyama et al.

[11] Patent Number: 5,847,123
[45] Date of Patent: Dec. 8, 1998

[54] IMIDE DERIVATIVES FOR INHIBITING THE PRODUCTION OF INTERLEUKIN-1β AND THE PRODUCTION OF TUMOR NECROSIS FACTOR α

[75] Inventors: Shinji Yokoyama; Noriyoshi Sueda; Hiroaki Yamada; Ryotaro Kojima, all of Saitama-ken; Koichi Katsuyama, Tokyo, all of Japan

[73] Assignee: Nisshin Flour Milling Co., Ltd., Tokyo, Japan

[21] Appl. No.: 886,540

[22] Filed: Jul. 1, 1997

[30] Foreign Application Priority Data

Jul. 2, 1996 [JP] Japan .................................. 8-172148

[51] Int. Cl.$^6$ .................. A61K 31/16; A61K 31/635; C07C 233/00; C07D 207/00; C07D 213/00; C07D 263/00

[52] U.S. Cl. ................... 540/529; 514/212; 514/352; 514/357; 514/376; 514/398; 514/423; 514/440; 514/466; 514/471; 514/616; 546/312; 546/337; 548/229; 548/318.5; 548/540; 549/77; 549/439; 549/496; 564/152; 564/155

[58] Field of Search .................. 548/229, 318.5, 548/540; 564/152, 155; 546/312, 337; 549/77, 439, 496; 540/529; 514/212, 352, 357, 376, 398, 423, 448, 466, 471, 616

[56] References Cited

U.S. PATENT DOCUMENTS

| 5,137,905 | 8/1992 | Moon et al. | ............................. 514/392 |
| 5,231,179 | 7/1993 | Terashima et al. | ..................... 540/200 |

FOREIGN PATENT DOCUMENTS

| 0321256 | 6/1989 | European Pat. Off. | ............... 548/540 |
| 0 720 849 | 7/1996 | European Pat. Off. . | |
| 60-11455 | 1/1985 | Japan | ...................................... 564/56 |
| 92/14455 | 9/1992 | WIPO . | |
| 94/10168 | 5/1994 | WIPO . | |
| 95/01348 | 1/1995 | WIPO . | |
| 96/20705 | 7/1996 | WIPO . | |
| 96/20926 | 7/1996 | WIPO . | |

*Primary Examiner*—Floyd D. Higel
*Attorney, Agent, or Firm*—Oblon, Spivak, McClelland, Maier & Neustadt, P.C.

[57] ABSTRACT

Imide compounds having a propioloyl group or pharmaceutically acceptable salts thereof which exhibit potent activities to inhibit the production of Interleukin 1-β and also the production of Tumor Necrosis Factor α. These imide compounds are useful as a prophylactic or therapeutic agent for inhibiting the production of Interleukin 1-β and the production of Tumor Necrosis Factor α, typically for such diseases as chronic rheumatism, sepsis, ulcerative colitis, Crohn's disease and many other related diseases in which Interleukin 1-β and/or Tumor Necrosis Factor α would participate.

10 Claims, No Drawings

IMIDE DERIVATIVES FOR INHIBITING THE PRODUCTION OF INTERLEUKIN-1β AND THE PRODUCTION OF TUMOR NECROSIS FACTOR α

FIELD OF THE INVENTION

This invention relates to novel imide derivatives and pharmaceutical compositions comprising as an active ingredient said imide derivatives or pharmaceutically acceptable salts thereof. More particularly, this invention is concerned with a new class of imide derivatives having a propioloyl group and pharmaceutically acceptable salts thereof as well as pharmaceutical compositions for inhibiting the production of Interleukin-1β (hereinafter referred to as IL-1β) and Tumor Necrosis Factor α (hereinafter referred to as TNFα) which comprises as an active ingredient at least one of the imide derivatives or pharmaceutically acceptable salts thereof, which are useful as a therapeutic agent for particularly chronic rheumatism, sepsis, ulcerative colitis or Crohn's disease.

BACKGROUND OF THE INVENTION

IL-1β and TNFα are a protein produced mainly from immunocompetent cells such as macrophages and neutrophils and an important factor for immune response. Also, they are known to be a factor playing a central role in the inflammatory process or a factor participating in many vital reactions in the hematopoiesis, internal secretion and nervous systems.

There has been recently clarified the relationship between IL-1β and inflammatory diseases such as chronic rheumatism. For instance, IL-1β and TNFβ were detected in the synovial membrane of patients suffering from chronic rheumatism. It is also reported that the IL-1β and TNFα levels in the synovial fluid correlate with observations on the local inflammation.

Presently, steroidal agents and non-steroidal antiinflammatory agents have been used for the treatment of inflammatory diseases such as chronic rheumatism. Steroidal agents can achieve remarkable improvement in various symptoms of inflammatory diseases, but they present the problems that drug tolerance may be developed by administration over a prolonged period of time and that side-effects, sometimes serious, such as gastrointestinal disturbance, dermatopathy, and nephritis may be caused. Non-steroidal antiinflammatory agents can temporarily inhibit inflammatory symptoms, but they can not radically cure inflammatory diseases.

DETAILED DESCRIPTION OF THE INVENTION

The present invention provides an imide compound of formula (I)

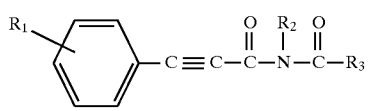

wherein, $R_1$ is hydrogen, halogen, trifluoromethyl or cyano;

$R_2$ is hydrogen, $C_1$–$C_4$ alkyl, di($C_1$–$C_4$)alkylamino($C_1$–$C_4$)alkyl, a group of formula (i)

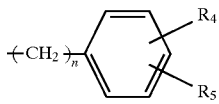

wherein n is an integer of 0–3, $R_4$ and $R_5$ each independently represent hydrogen, halogen, $C_1$–$C_4$ alkyl or $C_1$–$C_4$ alkoxy, or $R_4$ and $R_5$ jointly may be methylenedioxy or a group of formula (ii)

$$—(CH_2)—Het \quad (ii)$$

wherein n is an integer of 0–3 and Het represents a 5- or 6-membered heterocyclic group having nitrogen or oxygen as a hetero atom;

$R_3$ is $C_1$–$C_4$ alkyl, $C_1$–$C_4$ alkoxy($C_1$–$C_4$)alkyl, a group of formula (iii)

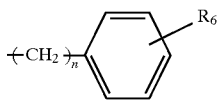

wherein n is an integer of 0–3, and $R_6$ is hydrogen or halogen or a 5- or 6-membered heterocyclic group having nitrogen, oxygen or sulfur as a hetero atom; or $R_2$ and $R_3$, together with a nitrogen atom to which $R_2$ is attached and a carbonyl group to which $R_3$ is attached, may form a heterocyclic group of formula (iv)

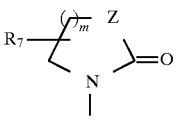

wherein m is an integer of 1–4, Z is —$CH_2$—, —NH— or —O—, $R_7$ is hydrogen, $C_1$–$C_4$ alkyl, $C_1$–$C_4$ alkoxycarbonyl or phenylpropioloyl or a pharmaceutically acceptable salt thereof.

The present invention also provides a process for the preparation of an imide compound of formula (I) which comprises reacting a carboxylic acid halide of formula (II)

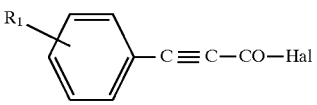

wherein $R_1$ is as defined above and Hal is halogen, with an amide compound of formula (III)

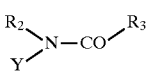

wherein $R_2$ and $R_3$ are as defined above and Y is an alkali metal atom or a trialkylsilyl group, to form an imide compound of formula (I) and if necessary, converting the imide compound of formula (I) to the corresponding pharmaceutically acceptable salt thereof.

The invention further provides a process for the preparation of an imide compound of formula (I) which comprises reacting a carboxylic acid halide of formula (II)

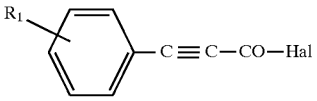

wherein $R_1$ is as defined above and Hal is halogen, with an amide compound of formula (IV)

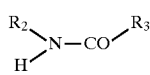

(IV)

wherein $R_2$ and $R_3$ are as defined above, in the presence of a base to form an imide compound of formula (I) and if necessary, converting the imide compound of formula (I) to the corresponding pharmaceutically acceptable salt thereof.

The invention still further provides a pharmaceutical composition which comprises as an active ingredient at least one of the imide compounds of formula (I) or a pharmaceutically acceptable salt thereof, and a pharmaceutically acceptable carrier. More particularly, the invention is concerned with a pharmaceutical composition for inhibiting the production of IL-1β and TNFα which comprises as an active ingredient at least one of the imide compounds of formula (I) or a pharmaceutically acceptable salt thereof, and a pharmaceutically acceptable carrier.

The term "halogen" as used herein includes fluorine, chlorine, bromine or iodine.

The term "$C_1$–$C_4$ alkyl" as used herein refers to a straight or branched alkyl group of 1–4 carbon atoms, which includes, for example, methyl, ethyl, n-propyl, isopropyl, n-butyl, isobutyl, sec-butyl and tert-butyl.

The term "$C_1$–$C_4$ alkoxy" as used herein refers to a straight or branched alkoxy of 1–4 carbon atoms, which includes, for example, methoxy, ethoxy, n-propoxy, isopropoxy, n-butoxy, isobutoxy, sec-butoxy and tert-butoxy.

The term "di($C_1$–$C_4$)alkylamino($C_1$–$C_4$)alkyl" as used herein refers to a dialkylaminoalkyl group wherein each alkyl moiety has 1–4 carbon atoms, which includes, for example, dimethylaminomethyl, dimethylaminoethyl, dimethylamino-n-propyl, dimethylamino-n-butyl, diethylaminomethyl, diethylaminoethyl, diethylaminoisopropyl, diethylamino-sec-butyl, di-n-propylaminomethyl, di-isopropylaminoethyl, di-n-propylamino-n-propyl and di-n-butylamino-n-butyl.

The term "$C_1$–$C_4$ alkoxy($C_1$–$C_4$)alkyl" as used herein refers to an alkoxyalkyl group wherein said alkoxy moiety has 1–4 carbon atoms and said alkyl moiety has 1–4 carbon atoms, which includes, for example, methoxymethyl, methoxyethyl, methoxy-n-propyl, methoxy-n-butyl, ethoxymethyl, ethoxyethyl, ethoxy-n-propyl, ethoxy-n-butyl, n-propoxymethyl, n-propoxyethyl, n-propoxy-isopropyl, n-propoxy-n-butyl, n-butoxymethyl, n-butoxyethyl, n-butoxy-n-propyl and n-butoxy-n-butyl.

The term "$C_1$–$C_4$ alkoxycarbonyl" as used herein refers to an alkoxycarbonyl group wherein said alkoxy moiety has 1–4 carbon atoms, which includes, for example, methoxycarbonyl, ethoxycarbonyl, n-propoxycarbonyl, isopropoxycarbonyl, n-butoxycarbonyl and tertbutoxycarbonyl.

The term "5- or 6-membered heterocyclic group having nitrogen or oxygen as a hetero atom" and the term "5- or 6-membered heterocyclic group having nitrogen, oxygen or sulfur as a hetero atom" refers to any of those 5- or 6-membered heterocyclic groups having at least one of the hetero atoms of N, O and S well-known in the art, which includes, for example, furyl, thienyl, pyrrolyl, oxazolyl, isooxazolyl, thiazolyl, isothiazolyl, pyrazolyl, pyridyl, pyrazinyl, pyridazinyl, piperidinyl, piperazinyl, pyranyl, thiopyranyl and morpholinyl.

In formula (I) or (iii), the substituent $R_1$ or $R_6$ may be attached to the phenyl moiety at any of o-, m- and p-positions to the propioloyl moiety or the alkylene moiety.

In formula (i) or (ii), the —$(CH)_n$— moiety when n is 1–3 may be a staright or branched alkylene of 1–3 carbon atoms, e.g., methylene, ethylene or propylene.

Specific examples of the imide compounds of this invention will be illustrated, without any limitation, as shown in the following Table 1 and Table 2.

TABLE 1

| Compound No. | $R_1$ | |
|---|---|---|
| 1 | H | |
| 2 | p-Cl | " |
| 3 | p-F | " |
| 4 | p-CN | " |
| 5 | p-CN | |
| 6 | p-F | " |
| 7 | H | " |
| 8 | H | |
| 9 | H | Me |
| 10 | H | |
| 11 | H | |

TABLE 1-continued

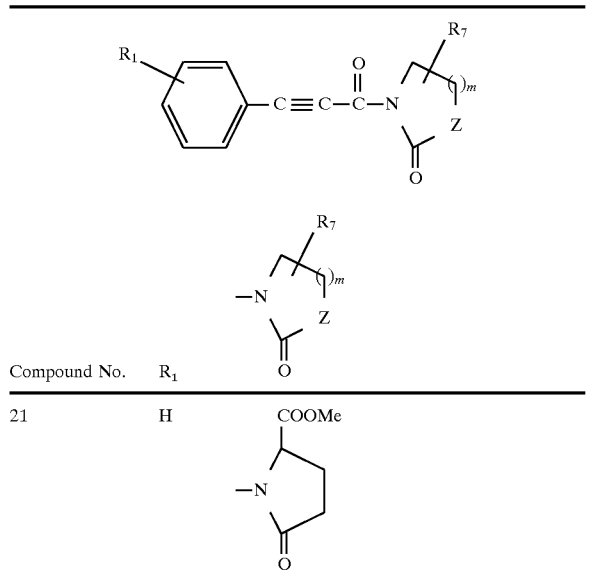

| Compound No. | R₁ | |
|---|---|---|
| 21 | H | COOMe (pyrrolidinone structure) |

TABLE 2

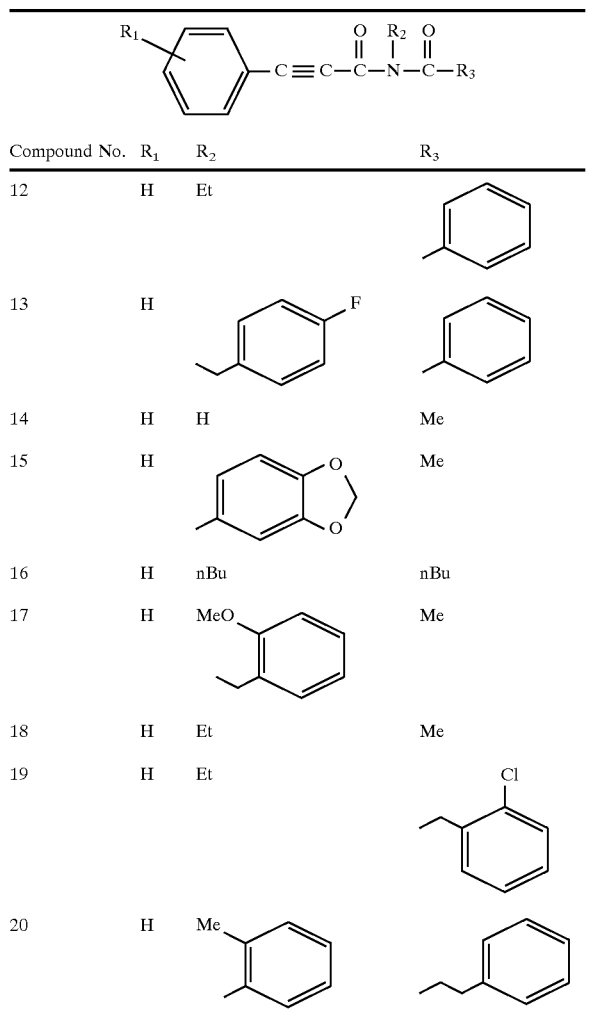

| Compound No. | R₁ | R₂ | R₃ |
|---|---|---|---|
| 12 | H | Et | phenyl |
| 13 | H | 4-F-benzyl | phenyl |
| 14 | H | H | Me |
| 15 | H | methylenedioxyphenyl-methyl | Me |
| 16 | H | nBu | nBu |
| 17 | H | 2-MeO-benzyl | Me |
| 18 | H | Et | Me |
| 19 | H | Et | 2-Cl-benzyl |
| 20 | H | 2-Me-benzyl | benzyl |

TABLE 2-continued

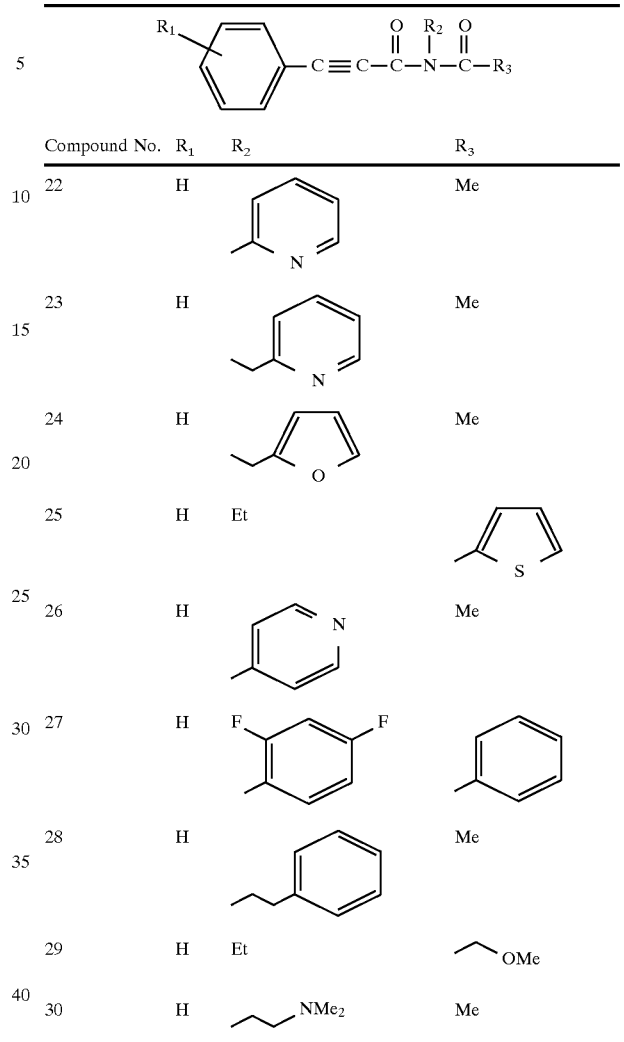

| Compound No. | R₁ | R₂ | R₃ |
|---|---|---|---|
| 22 | H | (2-pyridyl)methyl | Me |
| 23 | H | (2-pyridyl)ethyl | Me |
| 24 | H | (furan-2-yl)ethyl | Me |
| 25 | H | Et | thiophen-2-yl |
| 26 | H | (4-pyridyl)methyl | Me |
| 27 | H | 2,5-difluorobenzyl | phenyl |
| 28 | H | phenethyl | Me |
| 29 | H | Et | CH₂OMe |
| 30 | H | CH₂CH₂CH₂NMe₂ | Me |

The imide compounds of formula (I) of this invention can be prepared by reacting the carboxylic acid halide of formula (II) with the amide compound of formula (III), or by reacting the carboxylic acid halide of formula (II) with the amide compound of formula (IV) in the presence of a base. Both reactions may be carried out in a conventional manner known to a person skilled in the art.

The base which may be used in the reaction of the halide (II) and the amide compound (IV) may be any bases usually used for this reaction in the art, such as an alkaline or alkaline earth metal hydroxide, e.g., potassium or sodium hydroxide; an alkailne metal alkoxide, e.g., sodium methoxide; an alkaline or alkaline earth metal carbonate, e.g., potassium or sodium carbonate; an organic amine, e.g., pyridine or dimethylaniline; and the like.

The reaction parameters (such as reaction temperature, reaction time and others) for the two reactions may be any of those commonly used for these types of the reactions in the art.

One of the reactants, the carboxylic acid halide of the formula (II), may be easily prepared by reacting phenylpropiolic acid with a halogenating agent. This halogenation reaction may be carried out by reacting phenylpropiolic acid with the halogenating reagent preferably under the atmosphere of an inert gas such as argon, nitrogen and the like in the presence or absence of a solvent such as anhydrous benzene or anhydrous toluene under reflux.

The carboxylic acid halides which may be used herein may be, for example, a carboxylic acid fluoride, a carboxylic acid chloride, a carboxylic acid bromide, a carboxylic acid iodide. Typically used is a carboxylic acid chloride in view of easy availability of halogenating agents, its higher reactivity and other factors. For the synthesis of carboxylic acid chlorides, there may be desirably used such halogenating agents as oxalyl chloride, phosphorus pentachloride, phosphorus trichloride, thionyl chloride and the like. Halogenating agents for the synthesis of other carboxylic acid halides may be chosen correspondingly to those of the carboxylic acid chloride.

In the amide derivative of the formula (III), when Y is an alkali metal, it may be sodium, lithium, potassium and others and, when Y is a trialkylsilyl group, it may be those trialkylsilyl groups wherein said alkyl moiety is as defined above such as a trimethylsilyl, triethylsilyl or tripropylsilyl group. When the amide derivative of the formula (III) wherein Y is a trimethylsilyl group is used, silylation may be easily carried out, for example, by reacting the free amide derivative with 1–10 equivalents of hexamethylenedisilazane in the presence or absence of a solvent such as toluene and the like, preferably under reflux. The reaction of the carboxylic acid chloride with the trimethylsilylated amide derivative may be preferably carried out in the presence of a solvent at a temperature from 0° C. to a reflux temperature of the solvent used.

Examples of the solvents which may be used in the present reactions include an aromatic hydrocarbon such as benzene, toluene or xylene; an aliphatic hydrocarbon such as n-hexane or petroleum ether; an alicyclic hydrocarbon such as cyclohexane; a halogenated hydrocarbon such as carbon tetrachloride, chloroform, dichloroethane or trichloroethane; a cyclic ether such as tetrahydrofuran or dioxane; an ester such as ethyl acetate or butyl acetate; a ketone such as acetone or methyl ethyl ketone; dimethylformamide; dimethyl sulfoxide; and the like.

After completion of the reaction, the desired imide compound of formula (I) may be recovered and purified according to a conventional method.

The imide compounds of formula (I) according to this invention may be converted to the corresponding pharmaceutically acceptable acid addition salts, if desired. It is also contemplated that a pharmaceutical composition comprising the acid addition salts of the present imide compounds is included in the scope of this invention. Examples of the acid addition salts include those with inorganic acids such as hydrochloric acid, sulfuric acid, hydrobromic acid or phosphoric acid; organic sulfonic acids such as methanesulfonic acid, benezenesulfonic acid or p-toluenesulfonic acid; organic carboxylic acids such as acetic acid, propionic acid, oxalic acid, succinic acid, maleic acid, fumaric acid, lactic acid, tartaric acid, malic acid or citric acid.

The pharmaceutically acceptable acid addition salts of the imide compounds of formula (I) may be prepared according to a conventional method for forming an acid addition salt.

The imide compounds or pharmaceutically acceptable salts thereof according to this invention have a potent inhibitory activity on the production of IL-1β and also a potent inhibitory activity on the production of TNFα with a lower toxicity, thus being useful for the prophylaxis and treatment of those diseases in which IL-1β and/or TNFα would participate, for example, chronic rheumatism, osteoarthritis, sepsis, ulcerative colitis, Crohn's disease, Behcet's disease, systemic lupus erythematosus, scleroderma, multiple sclerosis, Kawasaki disease, Guillain-Barre syndrome, rejection in organ transplantation, nephritis, hepatitis, pancreatitis, periarteritis nodosa, cephalomeningitis, meningitis, periodontitis, burn, keloid, hypertrophic scar, corneal ulceration, psoriasis, urticaria, atopic dermatitis, pollen allergy, asthma, bronchitis, hyperventilation in adults, malaria, hemicrania, anorexia, Creutzfeldt-Jakob disease, osteoporosis, type II diabetes mellitus (NIDDM), gout, atherosclerosis, dialysis hypotension, cachexia by cancer or infectious disease, acquired immune deficiency syndrome (AIDS) and the like.

In particular, they are effective for the prophylaxis and treatment of chronic rheumatism, sepsis, colitis ulcerosa and crohn's disease.

The effective dose of the present imide compound or pharmaceutically acceptable salt thereof to exert its activity may be usually in the range of from 5 mg to 6 g, preferably 10 mg to 300 mg, daily for an adult. The active compound may be administered, for example, orally, intravenously, subcutaneously, intramuscularly, rectally or intraarticularly and preferably via oral, intraarticular or intravenous route.

The active compound may be formulated into a pharmaceutical preparation by a conventional method usually employed in the art.

The pharmaceutical preparation for oral administration includes tablets, granules, powders, hard capsules, soft capsules, oral solutions and the like.

The tablets or capsules to be orally administered may contain any conventional additives such as binders, e.g., crystalline cellulose, mannitol, dextrin, hydroxypropylcellulose, hydroxypropylmethylcellulose, polyvinylpyrrolidone, Macrogol (polyethylene glycol) and the like; excipients, e.g., lactose, corn starch, calcium phosphate, magnesium aluminum metasilicate and the like; lubricants, e.g., calcium stearate, talc and the like; disintegrators, e.g., carboxymethylcellulose and the like; and other additives. These preparations may be coated by a conventional coating method well-known in the art.

The liquid preparations to be orally administered may be aqueous or oily suspensions, emulsions, solutions, syrups, elixirs or other dosage forms, or they may be a dried product to be redissolved in water or other suitable vehicle before use. These liquid preparations may contain any additives commonly used in the art such as suspending agents, e.g., sorbitol syrup, carboxymethylcellulose, glucose/sugar syrup, gelatin, hydroxyethylcellulose, aluminum stearate gel, hardened oils and the like; emulsifying agents, e.g., lecithin, monooleic acid esters, sorbitan esters, acacia and the like; non-aqueous vehicles, e.g., palm oil, oily esters, propylene glycol, ethyl alcohol and the like; antiseptics, e.g., p-hydroxybenzoic acid esters, sorbic acid and the like; and others.

The preparation to be parenterally administered may be injections, suppositories and others. The injections may be prepared in a conventional manner by further adding, if desired, pH adjusters, buffers, stabilizers, preservatives, solubilizing agents and others.

This invention will be further illustrated by the following examples.

EXAMPLE 1

Preperation of Starting Materials
1) Synthesis of substituted phenylpropiolic acid
i) Synthesis of 4-halophenylpropiolic acid A mixture of 4-fluorobenzaldehyde (6.21 g), ethyl diethylphosphonoacetate (11.2 g), potassium carbonate (3.6 g) and methanol (60 ml) was refluxed for 2 hours. To the reaction mixture was added water, extracted with ethyl acetate and the solvent was distilled off to give 8.87 g of crude 4-fluorocinnamic acid ester (a mixture of the methyl ester and the ethyl ester). This crude product was dissolved in 60 ml of methylene chloride. The resulting solution was cooled to 0° C. and 2.7 ml of bromine was added dropwise and the mixture was allowed to react for one hour. Then, 2 ml of isoprene was added and the solvent was distilled off to give 16.3 g of an oily substance. This substance was dissolved in 60 ml of toluene, 11.0 g of potassium hydroxide was added portionwise under reflux and then refluxing was continued for further one hour. The reaction mixture was allowed to cool, water was added followed by stirring, the aqueous layer was separated and made acidic with diluted hydrochloric acid, the crystalline substance thus formed was filtered and crystallized successively with chloroform and then hot water to give 1.7 g of 4-fluorophenylpropiolic acid.

By repeating the same reaction procedures as described above using as the starting material 4-chlorobenzaldehyde was prepared 4-chlorophenylpropiolic acid.

ii) Synthesis of 4-cyanophenylpropiolic acid

Carbon tetrabromide (5.47 g) was dissolved in 50 ml of methylene chloride, cooled to 0° C., triphenylphosphine (8.66 g) was added, to the resulting orange solution was added 4-cyanobenzaldehyde (1.97 g) and the mixture was allowed to react at room temperature for one hour. The reaction mixture was concentrated and purified by a silica gel column chromatography to give 3.82 g of a crystalline substance. This substance was dissolved in 50 ml of anhydrous THF, 2 equivalents of n-butyl lithium was added at −78° C., allowed to rise to room temperature and the reaction was carried out for one hour. After cooling again to −78° C., the reaction mixture was further allowed to rise to room temperature. The reaction mixture was concentrated, the residue was dissolved in 5% aqueous sodium hydroxide, extracted with isopropyl ether, the aqueous layer was separated and made acidic with the addition of conc. hydrochloric acid, the crystalline substance and oily substance thus separated out were extracted with ethyl acetate and crystallized from ether to give 1.0 g of 4-cyanophenylpropiolic acid.

iii) Synthesis of phenylpropiolic chloride

Phenylpropiolic chloride was prepared by refluxing phenylpropiolic acid and an excess of thionyl chloride according to a conventional method, distilling off the thionyl chloride and then purifying with distillation.

EXAMPLE 2

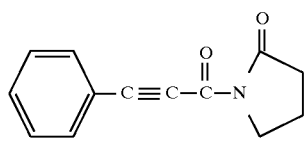
(Compound 1)

1) Synthesis (I)

A mixture of 2-pyrrolidone (2.13 g, 25 mmole) and hexamethyldisilazane (12.1 g, 75 mmole) was refluxed for 9 hours and an excess of hexamethyldisilazane was distilled off under reduced pressure to afford N-trimethylsilylated 2-pyrrolidone (hereinafter referred to as "TMS product of 2-pyrrolidone"). The resulting TMS product of 2-pyrrolidone was dissolved in 12 ml of toluene, phenylpropioloyl chloride (12.5 mmole) was added and refluxed. The reaction mixture was concentrated, the residue was dissolved in ethyl acetate, aqueous sodium hydrogencarbonate was added and the mixture was stirred for 0.5 hour. The ethyl acetate layer was separated, washed with saturated aqueous sodium chloride, dried and then the solvent was distilled off under reduced pressure, purified by silica gel column chromatography and crystallized from ether to give 1.25 g of Compound 1.

Yellow crystals, m.p. 97° C., $^1$H NMR (CDCl$_3$ δ) 7.65(2H, d, J=7.8 Hz), 7.45(1H, t, J=6.8 Hz), 7.36(2H, t, J=7.3 Hz), 3.89(2H, t, J=7.3 Hz), 2.65(2H, t, J=7.8 Hz), 2.10(2H, quintet, J=7.8 Hz)

2) Synthesis (II)

A solution of 2-pyrrolidone (2.13 g, 25 mmole) in 100 ml of anhydrous THF was cooled to −78° C. One equivalent of a hexane solution of n-butyl lithium was added dropwise, the mixture was allowed to rise to room temperature and the reaction was carried out for one hour. After cooling again to −78° C., phenylpropioloyl chloride (25 mmole) was added and the mixture was allowed to rise to room temperature and the reaction was carried out for one hour. Aqueous sodium hydrogencarbonate was added, the resulting mixture was stirred for 0.5 hour, 100 ml of ethyl acetate was added, the organic layer was separated and washed with saturated aqueous solution of sodium chloride, dried and then the solvent was distilled off under reduced pressure, purified by silica gel column chromatography, crystallized from ether to afford Compound 1.

EXAMPLE 3

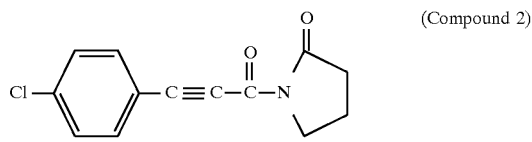
(Compound 2)

Compound 2 as prepared by refluxing 4-chlorophenylpropioloyl chloride and TMS product of 2-pyrrolidone in toluene and crystallizing from ether (Yield= 57% ).

Yellow crystals, m.p. 158° C.

$^1$H NMR (CDCl$_3$ δ) 7.60(2H, d, J=8.8Hz), 7.36(2H, d, J=8.3Hz), 3.89(2H, t, J=7.3 Hz), 2.66(2H, t, J=7.7 Hz), 2.11(2H, quintet, J=7.3 Hz)

EXAMPLE 4

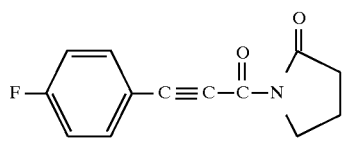
(Compound 3)

Compound 3 was prepared by refluxing 4-fluorophenylpropioloyl chloride and TMS product of 2-pyrrolidone in toluene, purifying by silica gel column chromatography and then crystallizing from methanol (Yield=48% ).

Colorless crystals, m.p. 158° C.

$^1$H NMR (CDCl$_3$ δ) 7.67(2H, dd, J=9.3, 6.1 Hz), 7.80(2H, t, J=8.8 Hz), 3.89(2H, t, J=7.3 Hz), 2.66(2H, t, J=7.8 Hz), 2.11(2H, q, J=7.4 Hz)

EXAMPLE 5

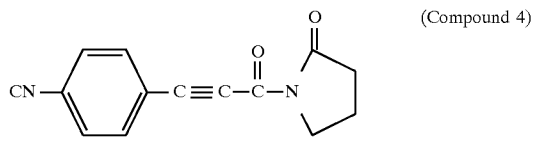
(Compound 4)

The Compound 4 was prepared by refluxing 4-cyanophenylpropioloyl chloride and TMS product of 2-pyrrolidone in toluene, purifying by silica gel column chromatography and crystallizing from methanol (Yield=14%).

Colorless crystals, m.p. 103° C.

$^1$H NMR (CDCl$_3$ δ) 7.74(2H, d, J=8.8 Hz), 7.68(2H, d, J=8.8 Hz), 3.90(2H, t, J=7.4 Hz), 2.67(2H, t, J=8.3 Hz), 2.13(2H, q, J=7.6 Hz)

EXAMPLE 6

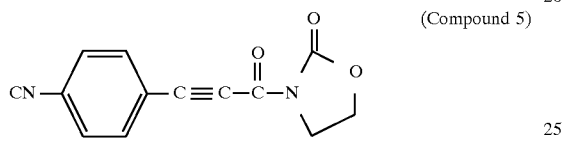
(Compound 5)

Compound 5 was prepared by refluxing 4-cyanophenylpropioloyl chloride and TMS product of 2-oxazolidone in toluene, purifying by silica gel column chromatography and crystallizing from methanol (Yield=56%).

Colorless crystals, m.p. 169° C.

$^1$H NMR (CDCl$_3$ δ) 7.76(2H, d, J=8.3 Hz), 7.68(2H, d, J=8.3 Hz), 4.49(2H, t, J=7.8 Hz), 4.11(2H, t, J=7.8 Hz)

EXAMPLE 7

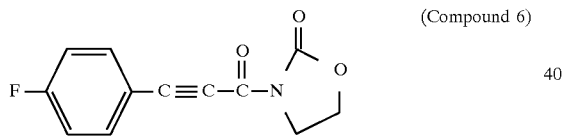
(Compound 6)

Compound 6 was prepared by refluxing 4-fluorophenylpropioloyl chloride and TMS product of 2-oxazolidone in toluene, purifying by silica gel column chromatography and crystallizing from methanol.

Colorless crystals, m.p. 149° C.

$^1$H NMR (CDCl$_3$ δ) 7.69(2H, dd, J=8.3, 5.3 Hz), 7.09(2H, t, J=8.8 Hz), 4.47(2H, t, J=7.8 Hz), 4.11(2H, t, J=7.8 Hz)

EXAMPLE 8

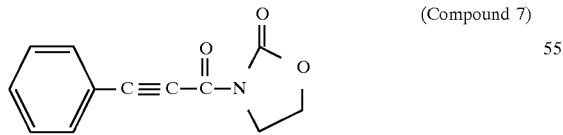
(Compound 7)

Compound 7 was prepared by refluxing phenylpropioloyl chloride and TMS product of 2-oxazolidone in toluene, purifying by silica gel column chromatography and crystallizing from methanol (Yield=56%).

Colorless crystals, m.p. 169° C.

$^1$H NMR (CDCl$_3$ δ) 7.68(2H, td, J=6.8, 1.5 Hz), 7.47(1H, tt, J=6.8, 1.5 Hz), 7.39(2H, tt, J=6.8, 1.5 Hz), 4.47(2H, t, J=8.3 Hz), 4.11(2H, t, J=8.3 Hz)

EXAMPLE 9

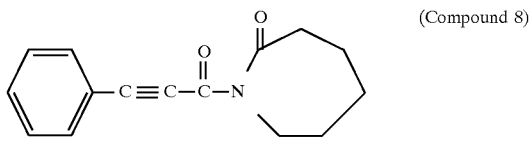
(Compound 8)

Compound 8 was prepared by refluxing phenylpropioloyl chloride and TMS product of ε-caprolactam in toluene and purifying by silica gel column chromatography (Yield=82%).

Yellow oily substance $^1$H NMR (CDCl$_3$ δ) 7.64(2H, dt, J=8.3, 2.0 Hz), 7.43(1H, tt, J=7.3, 2.4 Hz), 7.36(2H, tt, J=6.8, 1.4 Hz), 3.97(2H, t, J=5.1 Hz), 2.77(2H, t, J=4.6 Hz), 1.74–1.84(6H, m)

EXAMPLE 10

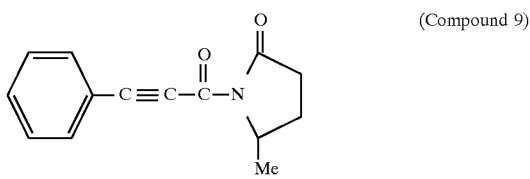
(Compound 9)

Compound 9 was prepared by refluxing phenylpropioloyl chloride and TMS product of 5-methyl-2-pyrrolidone in toluene, purifying by silica gel column chromatography and crystallizing from hexane (Yield=45%).

Yellow crystals, m.p. 79° C.

$^1$H NMR (CDCl$_3$ δ) 7.67(2H, dt, J=6.8, 1.5 Hz), 7.45(1H, tt, J=7.3, 1.5 Hz), 7.38(2H, tt, J=7.3, 1.5 Hz), 4.54(1H, qd, J=7.3, 2.0 Hz), 2.76(1H, quintet-d, J=8.8, 2.4 Hz), 2.56(1H, qd, J=8.8, 2.4 Hz), 2.24(1H, quintet-d, J=10.7, 3.4 Hz), 1.76(1H, tt, J=11.7, 2.0 Hz), 1.38(3H, d, J=6.8 Hz)

EXAMPLE 11

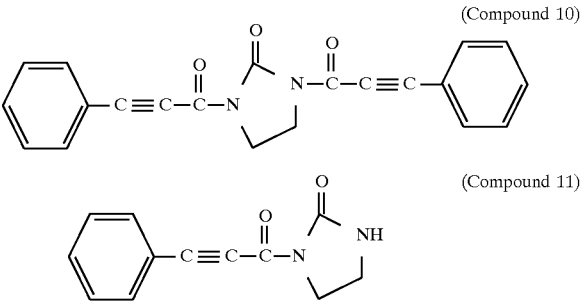
(Compound 10)

(Compound 11)

Compound 10 and Compound 11 with a high polarity were separated by refluxing phenylpropioloyl chloride and TMS product of propylene urea in toluene and purifying by silica gel column chromatography.

Data for Compound 10

Orange crystals, m.p. 204° C.

$^1$H NMR (CDCl$_3$ δ) 7.72(4H, dd, J=7.8, 2.0 Hz), 7.49(2H, tt, J=7.3, 2.0 Hz), 7.41(4H, t, J=7.8 Hz), 3.99(4H, s)

Data for Compound 11

Pale yellow crystals, m.p. 164° C.

$^1$H NMR (CDCl$_3$ δ) 7.66(2H, dd, J=6.3, 2.0 Hz), 7.44(1H, tt, J=7.8, 2.0 Hz), 7.37(2H, t, J=7.8 Hz ), 5.02(1H, brs), 4.05(2H, t, J=7.8 Hz), 3.56(2H, t, J=7.8 Hz)

EXAMPLE 12

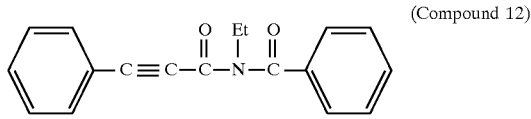
(Compound 12)

A mixture of TMS product of N-ethylbenzamide (1.81 g) and phenylpropioloyl chloride (1.0 g) in toluene was refluxed for 3.5 hours and worked up according to a conventional method and purified by silica gel column chromatography to give 0.47 g of Compound 12 as an oily substance (Yield=28%), which was then allowed to stand to crystallize.

Data for Compound 12 m.p. 64°–69° C.

$^1$H NMR (CDCl$_3$ δ) 7.72(2H, m), 7.2–7.55(6H, m), 7.10(2H, m), 4.07(2H, q), 1.35(2H, t)

IR(KBr cm$^{-1}$) 2212 1692 1659 1651 1351 1267 1110

MS 277(M+)

EXAMPLE 13

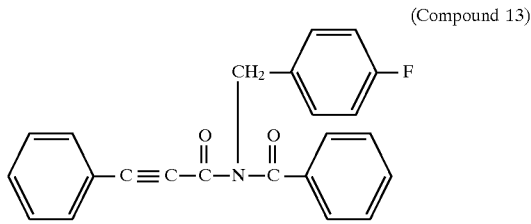
(Compound 13)

A mixture of TMS product of N-(4-fluorobenzyl)-benzamide (1.57 g and phenylpropioloyl chloride (1.0 g) in toluene was refluxed for 2 hours and worked up according to a conventional method and purified by silica gel column chromatography to give 0.60 g of Compound 13 as an oily substance (Yield=28%).

Data for Compound 13

$^1$H NMR (CDCl$_3$ δ) 7.66(2H, m), 7.4–7.54(5H), 7.34(1H, m), 7.24(2H, m), 7.03(4H, m), 5.16(2H, s)

IR(neat cm$^{-1}$) 2210 1694 1644 1510 1339 1094 965

MS 357(M+)

EXAMPLE 14

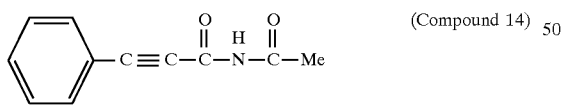
(Compound 14)

A mixture of N-trimethylsilylacetamide (1.0 g) and phenylpropioloyl chloride (1.0 g) in toluene was refluxed for 6 hours, worked up according to a conventional method, purified by silica gel column chromatography and recrystallized from chloroform-hexane to give 0.16 g of Compound 14 (Yield=14%).

Data for Compound 14 m.p. 103°–107.5° C.

$^1$H NMR (CDCl$_3$ δ) 8.36(1H, bs), 7.59(2H, m), 7.49(1H, m), 7.41(2H, m), 2.49(3H, m)

IR (KBr cm$^{-1}$) 2210 1715 1692 1667 1498 1376 1161 1028

EXAMPLE 15

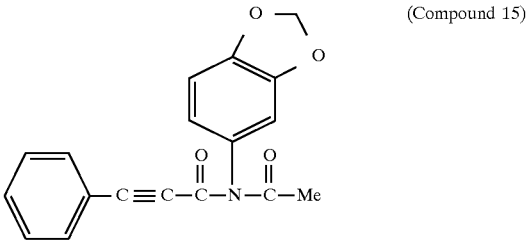
(Compound 15)

A mixture of TMS product of N-(3,4-methylenedioxyphenyl)acetamide (1.81 g ) (which was synthesized by refluxing the acetamide, HMDS and a small amount of DMF for 20 hours) and phenylpropioloyl chloride (1.0 g) in toluene was refluxed for 3 hours, worked up according to a conventional method, purified by silica gel column chromatography and recrystallized from chloroform-hexane to give 0.89 g of Compound 15 (Yield=48%).

Data for Compound 15 m.p. 129°–130° C.

$^1$H NMR (CDCl$_3$ δ) 7.2–7.43(5H), 6.90(1H, d), 6.76(2H, m), 6.05(2H, s), 2.62 (3H, s)

EXAMPLE 16

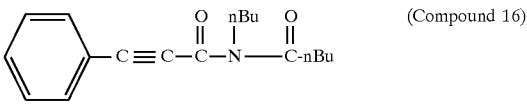
(Compound 16)

A mixture of TMS product of N-(n-butyl)-n-pentaneamide (1.5 g) and phenylpropioloyl chloride (0.9 g) in toluene was refluxed for 2 hours, worked up according to a conventional method, purified by silica gel column chromatography to give 0.39 g of Compound 16 as an oily substance (Yield=25%).

Data for Compound 16

$^1$H NMR (CDCl$_3$ δ) 7.57(2H, m), 7.49(1H, m), 7.41(2H, m), 4.00(2H, t), 2.93 (2H, t), 1.67(4H, m), 1.39(4H, m), 0.97(3H, t), 0.93(3H, t)

IR (neat cm$^{-1}$) 2210 1704 1671 1358 1186 1117

EXAMPLE 17

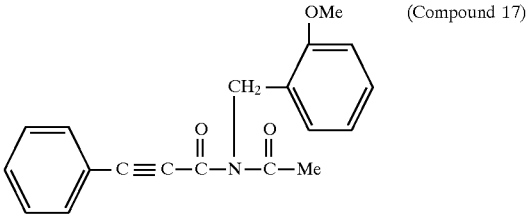
(Compound 17)

A mixture of TMS product of N-(2-methoxybenzyl) acetamide (1.4 g) (prepared by refluxing the acetamide and HMDS for 24 hours) and phenylpropioloyl chloride (1.0 g) in toluene was heated (90° C.) for one hour, worked up according to a conventional method, purified by silica gel column chromatography and recrystallized from chloroform-hexane to give 0.48 g of Compound 17 (Yield=26%).

Data for Compound 17 m.p. 126°–127.5° C.

¹H NMR (CDCl₃ δ) 7.2–7.45(6H), 7.08(1H, d), 6.92(1H, t), 6.86(1H, d), 5.24(2H, s), 3.82(3H, s), 2.63(3H, s)

EXAMPLE 18

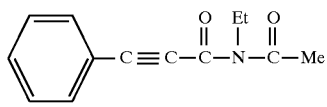
(Compound 18)

A mixture of TMS product of N-ethylacetamide (1.25 g) and phenylpropioloyl chloride (0.9 g) in toluene was heated (80° C.) for 2 hours, worked up according to a conventional method, purified by silica gel column chromatography and recrystallized from ether-hexane to give 0.31 g of Compound 18 (Yield=26%).

Data for Compound 18 m.p. 42°–43.5° C.

¹H NMR (CDCl₃ δ) 7.58(2H, m), 7.4–7.5(3H), 4.08(2H, q), 2.58(3H, s), 1.31(3H, t)

IR (KBr cm⁻¹) 2204 1698 1669 1357 1241 1102 765

EXAMPLE 19

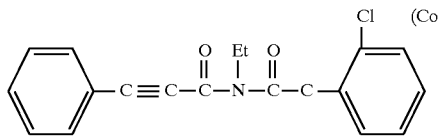
(Compound 19)

A mixture of TMS product of N-ethyl-2-chlorophenylacetamide (0.53 g) and phenylpropioloyl chloride (0.4 g) in toluene was refluxed for 8 hours, worked up according to a conventional method, purified by silica gel column chromatography and recrystallized from ether-hexane to give 0.12 g of Compound 19 (Yield=15%).

Data for Compound 19 m.p. 60°–61.5° C.

¹H NMR (CDCl₃ δ) 7.60(2H, m), 7.38–7.52(4H), 7.24 (3H, m), 4.37(2H, s), 4.13(2H, q), 1.34(3H, t)

EXAMPLE 20

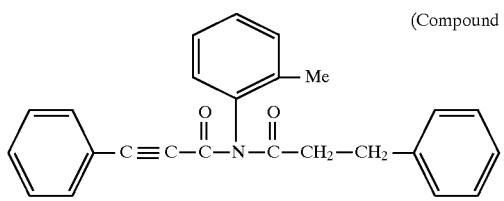
(Compound 20)

A mixture of TMS product of N-(2-methylphenyl)-3-phenylpropionamide (2.0 g) and phenylpropioloyl chloride (1.0 g) in toluene was heated (100° C.) for 2 hours, worked up according to a conventional method and purified by silica gel column chromatography to give 0.85 g of Compound 20 (Yield=35%).

Data for Compound 20

¹H NMR (CDCl₃ δ) 7.06–7.41(14H), 3.32(2H, t), 3.06 (2H, dt), 2.13(3H, s)

IR (neat cm⁻¹) 2208 1712 1676 1491 1306 1208 1132

EXAMPLE 21

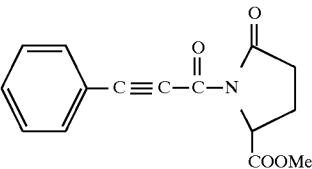
(Compound 21)

A mixture of phenylpropioloyl chloride and N-TMS-DL-pyroglutamic acid methyl ester in toluene was refluxed and purified by silica gel chromatography to give Compound 21 as a yellow oily substance (Yield=67%).

Data for Compound 21

¹H NMR (CDCl₃ δ) 7.68(2H, dd, J=7.2, 1.4 Hz), 7.47(1H, tt, J=7.7, 1.5 Hz), 7.39(2H, td, J=8.3, 1.4 Hz), 4.85(1H, dd, J=9.3, 2.6 Hz), 3.80(3H, s), 2.73–2.82(1H, m), 2.63(1H, qd, J=9.3, 3.0 Hz), 2.35–2.45(1H, m), 2.12–2.20(1H, m)

EXAMPLE 22

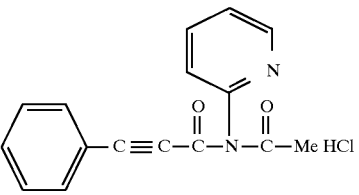
(Compound 22)

To a solution of 2-acetaminopyridine in anhydrous THF was added dropwise at −78° C. one equivalent of a n-butyl lithium solution in hexane, the resulting mixture was allowed to rise to room temperature and the reaction was carried out for one hour. After cooling again to −78° C., phenylpropioloyl chloride was added, the mixture was allowed to rise to room temperature and reacted for one hour. Aqueous sodium hydrogencarbonate was added, the mixture was stirred for 0.5 hour, extracted with ethyl acetate and the solvent was distilled off under reduced pressure, purified by silica gel column chromatography, crystallized from ethyl acetate-hexane. The crystalline substance was converted to the corresponding hydrochloride by a 4N-hydrochloric acid-ethyl acetate solution and recrystallized from ethanol to give Compound 22 (Yield=6%).

Data for Compound 22

Colorless crystals, m.p. 130° C. (dec.)

¹H NMR (DMSO) 8.38(1H, d, J=4.9 Hz), 8.02(1H, d, J=8.3 Hz), 7.86(1H, t, J=6.8 Hz), 7.68(2H, d, J=6.8 Hz), 7.48–7.57(3H, m), 7.54(1H, t, J=6.8 Hz), 2.50(3H, s)

EXAMPLE 23

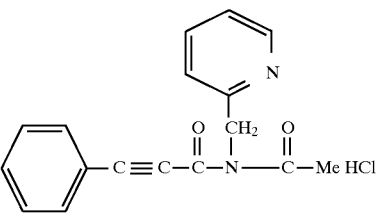
(Compound 23)

To a solution of 2-(acetaminomethyl)pyridine in anhydrous THF was added dropwise at −78° C. one equivalent of a n-butyl lithium solution in hexane, the resulting mixture was allowed to rise to room temperature and reacted for one hour. After cooling again to −78° C. phenylpropioloyl chloride was added, the mixture was allowed to rise to room temperature and reacted for one hour. Aqueous sodium hydrogencarbonate was added, the mixture was stirred for 0.5 hour, extracted with ethyl acetate and the solvent was distilled off under reduced pressure, purified by silica gel chromatography, crystallized from ethyl acetate-hexane. The crystalline substance was converted to the corresponding hydrochloride by a 4N hydrochloric acid-ethyl acetate solution in chloroform and crystallized from isopropyl alcohol to give Compound 23 (Yield=32%).

Data for Compound 23

Colorless crystals, m.p. 130° C. (dec.)

$^1$H NMR (DMSO) 8.66(1H, d, J=4.9 Hz), 8.10(1H, t, J=7.3 Hz), 7.68(1H, d, J=7.8 Hz), 7.53–7.58(3H, m), 7.53 (2H, t, J=7.8 Hz), 5.38(2H, s), 2.59(3H, s)

EXAMPLE 24

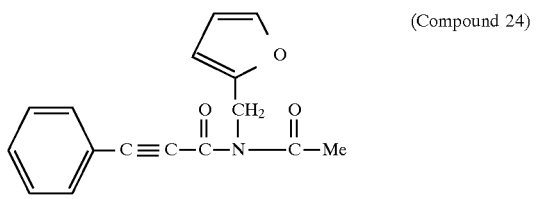

(Compound 24)

To a solution of 2-(acetaminomethyl)furan in anhydrous THF was added dropwise at −78° C. one equivalent of a n-butyl lithium solution in hexane, the resulting mixture was allowed to rise to room temperature and reacted for one hour. After cooling again to −78° C., phenylpropioloyl chloride was added, the mixture was allowed to rise to room temperature and reacted for one hour. Aqueous sodium hydrogencarbonate was added, the mixture was stirred for 0.5 hour, extracted with ethyl acetate and the solvent was distilled off under reduced pressure, purified by silica gel column chromatography to give Compound 24 (Yield= 47%).

Data for Compound 24

Yellow crystals, m.p. 42° C.

$^1$H NMR (CDCl$_3$ δ) 7.60(2H, dt, J=7.3, 1.5 Hz), 7.49(1H, tt, J=7.3, 2.0 Hz), 7.41(2H, t, J=7.3 Hz), 7.35(1H, t, J=1.4 Hz), 6.33–6.32(2H, m), 5.22(2H, s), 2.61(3H, s)

EXAMPLE 25

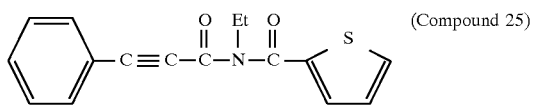

(Compound 25)

To a solution of 2-thienoylethylamide(thiophenecarbonylethylamide) in anhydrous THF was added dropwise at −78° C. one equivalent of a n-butyl lithium solution in hexane, the resulting mixture was allowed to rise to room temperature and reacted for one hour. After cooling again to −78° C., phenylpropioloyl chloride was added, the mixture was allowed to rise to room temperature and reacted for one hour. Aqueous sodium hydrogencarbonate was added, the mixture was stirred for 0.5 hour, extracted with ethyl acetate and the solvent was distilled off under reduced pressure, purified by silica gel chromatography to give Compound 25 as a brown substance (Yield=78%), which was crystallized on standing.

Data for Compound 25 m.p. 42° C.

$^1$H NMR (CDCl$_3$ δ) 7.80(1H, d, J=4.9 Hz), 7.66(1H, d, J=3.4 Hz), 7.38(1H, t, J=7.2 Hz), 7.28(2H, t, J=8.3 Hz), 7.20(2H, d, J=6.8 Hz), 7.11(1H, t, J=4.9 Hz), 4.01(2H, q, J=7.3 Hz), 1.34(3H, t, J=7.3 Hz)

EXAMPLE 26

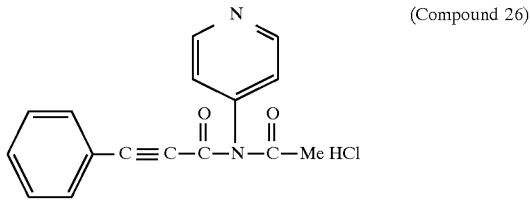

(Compound 26)

To a solution of 4-(acetaminomethyl)pyridine in anhydrous THF was added dropwise at −78° C. one equivalent of a n-butyl lithium solution in hexane, the resulting mixture was allowed to rise to room temperature and reacted for one hour. After cooling again to −78° C., phenylpropioloyl chloride was added, the mixture was allowed to rise to room temperature and reacted for one hour. Aqueous sodium hydrogencarbonate was added, the mixture was stirred for 0.5 hour, extracted with ethyl acetate and the solvent was distilled off under reduced pressure, purified by silica gel column chromatography, converted to the corresponding hydrochloride in chloroform using a 4N hydrochloric acid-ethyl acetate solution and crystallized from isopropyl alcohol to give Compound 26 (Yield=18%).

Data for Compound 26

Colorless crystals, m.p. 130° C. (dec.)

$^1$H NMR (DMSO) 8.96(1H, d, J=5.9 Hz), 7.93(1H, d, J=5.4 Hz), 7.53(1H, t, J=7.8 Hz), 7.42(2H, t, J=7.8 Hz), 7.22(2H, d, J=7.8 Hz), 2.57(3H, s)

EXAMPLE 27

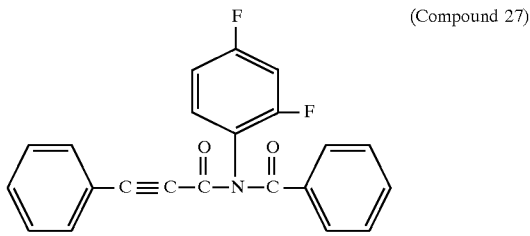

(Compound 27)

N-(2,4-Difluorophenyl)benzamide (1.45 g) was reacted with n-butyl lithium in THF and a solution of phenylpropioloyl chloride (1.0 g) in THF was added dropwise. The reaction mixture was worked up according to a conventional method and purified by silica gel column chromatography to give 0.77 g of Compound 27 as an oily substance (Yield= 35%).

Data for Compound 27

$^1$H NMR (CDCl$_3$ δ) 7.82(2H, m), 7.55(1H, m), 7.2–7.5 (8H, m), 6.99(2H, m)

IR (neat cm$^{-1}$) 2208 1699 1612 1509 1268 1198 1174 1144 964 759

EXAMPLE 28

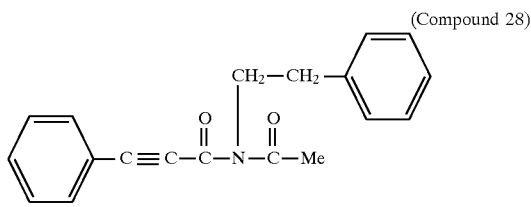
(Compound 28)

TMS product of N-phenethylacetamide (1.9 g) was reacted with phenylpropioloyl chloride (1.2 g) under heating (100° C.) in toluene for 2 hours. The reaction mixture was worked up according to a conventional method and purified by silica gel column chromatography to give 0.60 g of Compound 28 as an oily substance (Yield=34%), which crystallized on standing.

Data for Compound 28 m.p. 58°–65° C.

$^1$H NMR (CDCl$_3$ δ) 7.56(2H, m), 7.50(1H, m), 7.42(2H, m), 7.25(5H), 4.23(2H, m), 2.98(2H, t), 2.59(3H, s)

IR (KBr cm$^{-1}$) 2205 1703 1668 1660 1354 1250 1168 1155 764

EXAMPLE 29

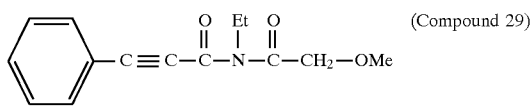
(Compound 29)

N-Ethylmethoxyacetamide (0.77 g) was reacted with n-butyl lithium in THF according to a conventional method and then reacted with phenylpropioloyl chloride (1.0 g). The reaction mixture was worked up according to a conventional method, purified by silica gel column chromatography and recrystallized from ether-hexane to give 0.79 g of Compound 29 (Yield=53%).

Data for Compound 29 m.p. 87°–88.0° C.

$^1$H NMR (CDCl$_3$ δ) 7.59(2H, m), 7.49(1H, m), 7.42(2H, m), 4.57(2H, s), 3.49(3H, s), 3.13(2H, q), 1.34(3H, t)

IR (KBr cm$^{-1}$) 2212 1718 1663 1374 1209 1198 1107 770

EXAMPLE 30

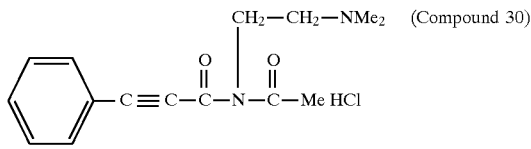
(Compound 30)

N-(2-(N,N-Dimethylamino)ethyl)acetamide (1.52 g) was reacted with n-butyl lithium in THF according to a conventional method and then reacted with phenylpropioloyl chloride (1.2 g). The reaction mixture was worked up according to a conventional method to give 1.55 g of the residue. This residue showed tailing (CHCl$_3$—MeOH) on a silica gel plate and decomposition was clearly confirmed by the 2D development. The residue was purified by silica gel column chromatography to give 0.40 g of the desired free base as an oily substance (Yield=21%), which crystallized on standing.

Data for Compound 30

$^1$H NMR (CDCl$_3$ δ) 7.58(2H, m), 7.49(1H, m), 7.41(2H, m), 4.11(2H, t), 2.57(3H, s), 2.55(2H, t), 2.30(6H, s)

IR (KBr cm$^{-1}$) 2214 2198 1701 1662 1354 1243 1151 1073 975 762

The crystal thus obtained was dissolved in chloroform and converted to the corresponding hydrochloride by the addition of 0.40 ml of a 4N hydrochloric acid-acetic acid solution to give Compound 30. Crystallization of this compound was tried, but unsuccessfully and a syrupy product was obtained.

Test Example 1

Determination for the inhibitory activity of the IL-1β production and the inhibitory activity of the TNFα production The THP-1 cells, which is the monocyte-established cell line derived from human peripheral blood (ATCC TIB202), were incubated at 37° C. in a 5% CO$_2$ incubator in RPMI 1640 medium (available from Bio-Whittaker Co., Ltd.) containing 10% (v/v) of fetal bovine serum, 2 mM of glutamine, 50 μM of 2-mercaptoethanol, 60 μg/ml of penicillin and 100 μg/ml of streptomycin. The THP-1 cells maintained as described above were centrifuged at 1200 rpm at room temperature for 3 minutes to recover the cells in a 50 ml conical tube. The cell pellets thus obtained were resuspended in RPMI 1640 medium containing 2% (v/v) of fetal bovine serum and the glutamine, 2-mercaptoethanol and antibiotics as described above so as to provide a final THP-1 cell concentration of 2×10$^6$ cells/ml.

The cell resuspension having the above concentration was dispensed in 0.5 ml portions to a 24-well plate for cell culture. Then, 2.5 μl each of the solutions of the present imide derivatives dissolved in DMSO was added to each well. The plate was then incubated at 37° C. in a 5% CO$_2$ incubator for one hour. Then, 12-o-tetradecanoylphorbol-13-acetate (hereinafter referred to as PMA) and polyinosic acid were added to each well so as to provide the final concentrations of 2 μg/ml and 200 μg/ml, respectively. The plate was further incubated at 37° C. in a 5% CO$_2$ incubator for 22 hours and the IL-1β and TNFα produced in the cultured broth were assayed. The assay for IL-1β was carried out by means of the enzyme immunoassay kit available from Cayman Chemical Co., Ltd., while the assay of TNFα was done by means of the ELIZA kit available from Genzyme Co., Ltd.

The inhibitory activity was expressed in terms of IC$_{50}$ values, wherein the produced amount of IL-1β and the produced amount of TNFα when no imide derivative was added are defined as 100, respectively, and the concentration of each imide derivative of the present invention to inhibit the IL-1β production and TNFα production is defined as IC$_{50}$, respectively. The results are shown in Table 3.

TABLE 3

| | IC$_{50}$ | |
| --- | --- | --- |
| Test Compound (Compound No.) | IL-1β (μM) | TNFα (μM) |
| 1 | 1.4 | 1.0 |
| 2 | 5.5 | 1.6 |
| 3 | 3.8 | 1.3 |
| 4 | 7.0 | 1.7 |
| 5 | 2.6 | 2.1 |
| 6 | 2.4 | 1.7 |
| 7 | 1.1 | 1.2 |
| 8 | 6.0 | 2.1 |
| 9 | 2.8 | 0.9 |
| 10 | 6.7 | 0.5 |
| 11 | 1.8 | 0.5 |
| 12 | 9.6 | 5.4 |
| 13 | 15 | 15 |

TABLE 3-continued

| Test Compound (Compound No.) | IC$_{50}$ | |
|---|---|---|
| | IL-1β (μM) | TNFα (μM) |
| 14 | 4.4 | 1.8 |
| 15 | 6.3 | 1.7 |
| 16 | 13 | 14 |
| 17 | 3.1 | 1.8 |
| 18 | 5.7 | 4.4 |
| 19 | 2.0 | 1.3 |
| 20 | 1.3 | 1.9 |
| 21 | 7.0 | 0.6 |
| 22 | 12 | 14 |
| 24 | 10 | 4.4 |
| 25 | >30 | 4.8 |
| 26 | 8.8 | 1.7 |
| 27 | 14 | 3.0 |
| 28 | 8.8 | 1.7 |
| 29 | >30 | >30 |
| 30 | 6.3 | 3.7 |

Test Example 2

Determination for Cytotoxicity The THP-1 cells, which is the monocyte-established cell line derived from human peripheral blood (ATCC TIB202), were incubated at 37° C. in a 5% $CO_2$ incubator in RPMI 1640 medium (available from Bio-Whittaker Co., Ltd.) containing 10% (v/v) of fetal bovine serum, 2 mM of glutamine, 50 μM of 2-mercaptoethanol, 60 μg/ml of penicillin and 100 μg/ml of streptomycin. The THP-1 cells maintained as described above were centrifuged at 1200 rpm at room temperature for 3 minutes to recover the cells in a 50 ml conical tube. The cell pellets thus obtained were suspended in RPMI 1640 medium containing 2% (v/v) of fetal bovine serum, 2 mM of glutamine, 50 μM of 2-mercaptoethanol, 60 μg/ml of penicillin and 100 μg/ml of streptomycin so as to provide the final cell concentration of 1×10$^6$ cells/ml.

The cell suspension obtained as above was dispensed in 1 ml portions to a 24-well plate for cell culture. Then, 5 μl each of the solutions of the present imide derivatives dissolved in DMSO was added to each well. The plate was then incubated at 37° C. in a 5% $CO_2$ incubator for 24 hours. After incubation, 100 μl of Alamar Blue (available from Biosource Co., Ltd.) was added to each well and then the plate was further incubated at 37° C. in a 5% $CO_2$ incubator for 3 hours. Thereafter, a supernatant was recovered and determined for a difference in absorbances at 570 nm and 600 nm. Cytotoxicity was then evaluated in accordance with the survival rates determined from the differences in absorbances. More specifically, the lethal dose for 50% (LD$_{50}$) in the THP-1 cells were calculated. The results are shown in Table 4.

TABLE 4

| Test Compound | LD$_{50}$ (μM) |
|---|---|
| Compound 1 | 70 |
| Compound 3 | >100 |
| Compound 6 | >100 |
| Compound 7 | >200 |
| Compound 8 | >200 |
| Compound 9 | 110 |

Test Example 3

Determination for the inhibitory activity of the TNFα production

To the DBA/2 strain mice previously given with LPS 5.6 mg/kg, i.v. were intraperitoneally administered twice before and after 30 minutes from the LPS administration the present imide derivatives selected from Compound 1, Compound 3, Compound 7, Compound 8, Compound 9 and Compound 26. After 2 hours from the LPD administration, the blood TNFα level was determined to investigate the inhibitory activity of the present imide derivatives on the TNFα production. More specifically, the blood TNFα level was determined when the present imide derivative was given at a dose of 10 mg/kg to calculate the inhibitory rate of the TNFα production.

The results are shown in Table 5. It was confirmed that all of Compounds 1, 3, 7, 8, 9 and 26 exhibit a significant inhibitory activity.

TABLE 5

| Test Compound | Inhibitory rate (%) of TNFα production |
|---|---|
| Compound 1 | 22 |
| Compound 3 | 37 |
| Compound 7 | 22 |
| Compound 8 | 31 |
| Compound 9 | 29 |
| Compound 26 | 37 |

Preparation Example 1

Tablets

Tablets were prepared using the following formulation per tablet:

| Tablet Formulation | |
|---|---|
| Compound 9 | 20 mg |
| Magnesium silicate | 20 mg |
| Lactose | 98.5 mg |
| Hydroxypropylcellulose | 7.5 mg |
| Magnesium stearate | 1 mg |
| Hardened vegetable oil | 3 mg |
| Total | 150 mg |

Compound 9, magnesium silicate and lactose were blended and kneaded with an alcoholic solution of hydroxypropylcellulose. The resulting mixture was granulated to an appropriate particle size, dried and sized. Then, magnesium stearate and hardened vegetable oil were blended to form uniform granules and then the granules were formed to tablets by means of a rotary tableting machine, each tablet having a diameter of 7.0 mm, a weight of 150 mg and a hardness of 6 kg.

Preparation Example 2

Granules

Granules were prepared using the following formulation:

| Granule Formulation | |
|---|---|
| Compound 9 | 10 mg |
| Magnesium oxide | 40 mg |
| Calcium hydrogenphosphate | 38 mg |
| Lactose | 10 mg |
| Hydroxypropylcellulose | 20 mg |

All components listed in the above Formulation except for the hydroxypropylcellulose were blended and then kneaded with an alcoholic solution of hydroxypropylcellulose. The resulting mixture was granulated by means of an extrusion granulating machine and then dried to form granules, which were then sized and passed through a 12 mesh sieve. The product left on a 48 mesh sieve was applied as granules.

Preparation Example 3
Syrups

Syrups were prepared using the following formulation:

| Syrup Formulation | |
|---|---|
| Compound 9 | 1.000 g |
| Sucrose | 30.000 g |
| 70 w/v % D-Sorbitol | 25.000 g |
| Ethyl p-hydroxybenzoate | 0.030 g |
| Propyl p-hydroxybenzoate | 0.015 g |
| Flavoring agent | 0.200 g |
| Glycerol | 0.150 g |
| 96% Ethanol | 0.500 g |
| Purified water | ad lib. |
| Total | 100 ml |

Sucrose, D-sorbitol, ethyl p-hydroxybenzoate, propyl p-hydroxybenzoate, and Compound 9 were dissolved in purified water (warm water). After cooling, a solution of the flavoring agent in glycerol and 96% ethanol was added. To the resulting mixture was added purified water to make it up to 100 ml.

Preparation Example 4
Injections

Injections were prepared using the following formulation:

| Injection Formulation | |
|---|---|
| Hydrochloride of Compound 26 | 10.0 mg |
| Sodium chloride | 81.0 mg |
| Sodiuin bicarbonate | 8.40 mg |
| Distilled water for injection | ad lib. |
| Total | 10.0 ml |

Sodium bicarbonate, sodium chloride and hydrochloride of Compound 26 were dissolved in distilled water for injection to make up a total volume to 10.0 ml.

Preparation Example 5
Suppositories

Suppositories were prepared using the following formulation:

| Suppository Formulation | |
|---|---|
| Compound 9 | 2 g |
| Macrogol 4000 (Polyethylene glycol 4000) | 20 g |
| Glycerol | 78 g |
| Total | 100 g |

Compound 9 was dissolved in glycerol and then Macrogol 4000 was added thereto. The resulting mixture was melted with heating, poured into a suppository mold and then solidified by cooling to form suppositories, each weighing 1.5 g.

What is claimed is:

1. An imide compound having the formula (I)

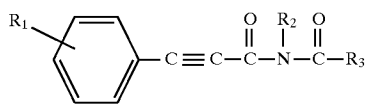

wherein, $R_1$ is hydrogen, halogen, trifluoromethyl or cyano;

$R_2$ is hydrogen, $C_1$–$C_4$ alkyl, di($C_1$–$C_4$)alkylamino($C_1$–$_4$)alkyl, a group of formula (i)

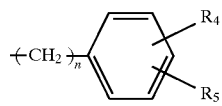

(i)

wherein n is an integer of 0–3, $R_4$ and $R_5$ each independently represent hydrogen, halogen, $C_1$–$C_4$ alkyl or $C_1$–$C_4$alkoxy, or $R_4$ and $R_5$ jointly are a meth group of formula (ii)

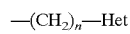

(ii)

wherein n is an integer of 0–3 and Het represents a 5- or 6-membered heterocyclic group having nitrogen or oxygen as a hetero atom;

$R_3$ is $C_1$–$C_4$ alkyl, $C_1$–$C_4$ alkoxy($C_1$–$C_4$)alkyl, a group of formula (iii)

(iii)

wherein n is an integer of 0–3, and $R_6$ is hydrogen or halogen or a 5- or 6-membered heterocyclic group having nitrogen, oxygen or sulfur as a hetero atom; or $R_2$ and $R_3$ together with a nitrogen atom to which $R_2$ is attached and a carbonyl group to which $R_3$ is attached form a heterocyclic group of formula (iv)

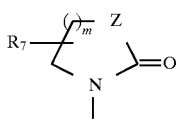

(iv)

wherein m is an integer of 1—4, Z is —$CH_2$—, —NH— or —O—, and $R_7$ is hydrogen, $C_1$–$C_4$ alkyl, $C_1$–$C_4$ alkoxycarbonyl or phenylpropioloyl or a pharmaceutically acceptable salt thereof.

2. The compound of claim 1 wherein $R_1$ is hydrogen, halogen, trifluoromethyl or cyano, and $R_2$ and $R_3$, together with a nitrogen atom to which $R_2$ is attached and a carbonyl group to which $R_3$ is attached, form a heterocyclic group of formula (iv) wherein m is 1 or 2, Z is —$CH_2$— or —NH— and $R_7$ is hydrogen, $C_1$–$C_4$ alkoxycarbonyl or phenylpropioloyl.

3. The compound of claim 1 wherein $R_1$ is hydrogen, $R_2$ is hydrogen, $C_1$–$C_4$ alkyl or di($C_1$–$C_4$)alkylamino($C_1$–$C_4$) alkyl, and $R_3$ is $C_1$–$C_4$ alkyl or ($C_1$–$C_4$)alkoxy($C_1$–$C_4$)alkyl.

4. The compound of claim 1 wherein $R_1$ is hydrogen, $R_2$ is a group of formula (i) wherein n is 0, 1 or 2, $R_4$ and $R_5$ each independently represent hydrogen, halogen, $C_1$–$C_4$ alkyl or $C_1$–$C_4$ alkoxy and $R_3$ is a group of formula (iii) wherein n is 0, 1 or 2, $R_6$ is hydrogen or halogen.

5. The compound of claim 1 wherein $R_1$ is hydrogen, $R_2$ is a group of formula (i) wherein $R_4$ and $R_5$ jointly represent methylenedioxy, and $R_3$ is $C_1$–$C_4$ alkyl.

6. The compound of claim 1 wherein $R_1$ is hydrogen, $R_2$ is a group of formula (ii) wherein n is 0 or 1 and Het represents furyl or pyridyl and $R_3$ is $C_1$–$C_4$ alkyl.

7. The compound of claim 1 wherein $R_1$ is hydrogen, $R_2$ is $C_1$–$C_4$ alkyl and $R_3$ is thienyl.

8. A pharmaceutical composition which comprises as an active ingredient an imide compound of formula (I) or a pharmaceutically acceptable salt thereof as claimed in any one of claims 1 to 7, and a pharmaceutically acceptable carrier.

9. The pharmaceutical composition of claim 8, wherein it is an agent for inhibiting the production of Interleukin-1β and the production of Tumor Necrosis Factor α.

10. The pharmaceutical composition of claim 8 wherein it is a therapeutic agent for chronic rheumatism, sepsis, ulcerative colitis or Crohn's disease.

* * * * *

UNITED STATES PATENT AND TRADEMARK OFFICE
CERTIFICATE OF CORRECTION

PATENT NO. : 5,847,123

DATED : December 8, 1998

INVENTOR(S): Shinji Yokoyama et al.

It is certified that an error appears in the above-identified patent and that said Letters Patent is hereby corrected as shown below:

Column 24, line 14 "meth" should read --methylenedioxy or a--.

Signed and Sealed this

Twenty-fifth Day of May, 1999

Attest:

Q. TODD DICKINSON

*Attesting Officer*    *Acting Commissioner of Patents and Trademarks*